US006566144B1

(12) United States Patent
Madril et al.

(10) Patent No.: US 6,566,144 B1
(45) Date of Patent: May 20, 2003

(54) COVER PLATE FOR USE IN LYOPHILIZATION

(75) Inventors: Dominic G. Madril, Loveland, CO (US); Cody L Yarborough, Ft. Collins, CO (US); Rajan Bawa, Ft. Collins, CO (US); Christopher J. Barrett, Ft. Collins, CO (US)

(73) Assignee: Atrix Laboratories, Fort Collins, CO (US)

( * ) Notice: Subject to any disclaimer, the term of this patent is extended or adjusted under 35 U.S.C. 154(b) by 0 days.

(21) Appl. No.: 09/535,846

(22) Filed: Mar. 27, 2000

(51) Int. Cl.$^7$ ................................................. G01N 1/18
(52) U.S. Cl. ........................................ 436/177; 436/174
(58) Field of Search ................................. 436/174–180; 422/99–104; 34/284–299

(56) References Cited

U.S. PATENT DOCUMENTS

| | | | |
|---|---|---|---|
| 2,353,986 A | | 7/1944 | Barr .................................. 34/5 |
| 3,454,178 A | * | 7/1969 | Bender et al. ............... 215/277 |
| 4,030,498 A | | 6/1977 | Tompkins ............... 128/218 P |
| 4,040,421 A | | 8/1977 | Young ..................... 128/218 N |
| 4,172,457 A | * | 10/1979 | Choksi et al. ........... 128/272.1 |
| 4,188,949 A | | 2/1980 | Antoshkiw ............. 128/218 M |
| 4,240,426 A | | 12/1980 | Akhavi .................... 128/218 N |
| 4,250,139 A | * | 2/1981 | Luck et al. ..................... 422/21 |
| 4,286,389 A | | 9/1981 | Ogle ................................ 34/5 |
| 4,452,473 A | | 6/1984 | Ruschke ........................ 285/81 |
| 4,501,719 A | | 2/1985 | Williams ...................... 422/102 |
| 4,631,055 A | | 12/1986 | Redl et al. ..................... 604/82 |
| 4,673,396 A | | 6/1987 | Urbaniak ..................... 604/211 |
| 4,729,208 A | * | 3/1988 | Galy et al. ..................... 53/432 |
| 4,743,229 A | | 5/1988 | Chu .............................. 604/82 |
| 4,758,230 A | | 7/1988 | Rycroft ....................... 604/118 |
| 4,766,908 A | | 8/1988 | Clement ..................... 128/765 |
| 4,829,006 A | * | 5/1989 | Smith et al. ................. 435/301 |
| 4,938,763 A | | 7/1990 | Dunn et al. ............... 604/891.1 |
| 4,978,336 A | | 12/1990 | Capozzi et al. ................ 604/82 |

(List continued on next page.)

FOREIGN PATENT DOCUMENTS

| | | | |
|---|---|---|---|
| CA | 2254361 | 5/1999 | ............ A61M/5/31 |
| DE | 3311525 | 10/1984 | ............ F26B/5/06 |
| DE | 19702564 | 9/1998 | ............ F25D/3/10 |

(List continued on next page.)

OTHER PUBLICATIONS

"Lyophilization", *McGraw–Hill Concise Encyclopedia of Science & Technology, Fourth Edition*, Sybil P. Parker, Editor in Chief, p. 1128, (1998).

*Primary Examiner*—Jill Warden
*Assistant Examiner*—Yelena Gakh
(74) *Attorney, Agent, or Firm*—Schwegman, Lundberg, Woessner & Kluth, P.A.

(57) ABSTRACT

The present invention provides a cover plate that covers one or more delivery containers (e.g., syringe) during lyophilization. The cover plate includes a lid region and one or more protuberances which project perpendicularly from the lid region. The one or more protuberances are adapted to fit in the one or more delivery containers. The cover plate permits the escape of vapor from the one or more delivery containers during the lyophilization process. In addition, the cover plate prevents the escape of lyophilizate from the one or more delivery containers during the lyophilization process. The present invention also provides a system for lyophilizing a solution that contains a pharmaceutical. The system includes one or more delivery containers. The one or more delivery containers contains the solution that contains the pharmaceutical. The system also includes a cover plate used to cover the one or more delivery containers during the lyophilization. The present invention also provides a method for lyophilizing a solution that contains a pharmaceutical. The method includes depositing the solution in one or more delivery containers, covering the one or more delivery containers with a cover plate, and lyophilizing the solution comprising the pharmaceutical.

10 Claims, 7 Drawing Sheets

U.S. PATENT DOCUMENTS

| | | | | |
|---|---|---|---|---|
| 4,994,029 A | | 2/1991 | Rohrbough | 604/88 |
| 5,000,737 A | * | 3/1991 | Free et al. | 604/110 |
| 5,005,721 A | * | 4/1991 | Jordan | 220/23.4 |
| 5,116,315 A | | 5/1992 | Capozzi et al. | 604/82 |
| 5,234,529 A | | 8/1993 | Johnson | 156/345 |
| 5,278,201 A | | 1/1994 | Dunn et al. | 523/113 |
| 5,279,608 A | * | 1/1994 | Cherif-Cheikh | 604/892.1 |
| 5,324,519 A | | 6/1994 | Dunn et al. | 424/426 |
| 5,352,756 A | * | 10/1994 | Meldal | 525/50 |
| 5,487,897 A | | 1/1996 | Polson et al. | 424/426 |
| 5,489,266 A | | 2/1996 | Grimard | 604/89 |
| 5,542,935 A | * | 8/1996 | Unger et al. | 604/190 |
| 5,556,279 A | | 9/1996 | Wolf et al. | 433/82 |
| 5,566,729 A | | 10/1996 | Grabenkort et al. | 141/25 |
| 5,595,760 A | * | 1/1997 | Cherif-Cheikh | 424/464 |
| 5,599,552 A | | 2/1997 | Dunn et al. | 424/423 |
| 5,653,693 A | * | 8/1997 | Miwa et al. | 604/187 |
| 5,660,849 A | | 8/1997 | Polson et al. | 424/426 |
| 5,770,559 A | * | 6/1998 | Manning et al. | 514/2 |
| 5,779,668 A | | 7/1998 | Grabenkort | 604/89 |
| 5,807,345 A | * | 9/1998 | Grabenkort | 604/199 |
| 5,882,603 A | * | 3/1999 | Taggart | 422/104 |
| 5,893,842 A | | 4/1999 | Imbert | 604/110 |
| 5,900,422 A | * | 5/1999 | Ali | 514/316 |
| 5,908,054 A | | 6/1999 | Safabash et al. | 141/26 |
| 5,928,215 A | | 7/1999 | Caizza et al. | 604/411 |
| 5,947,933 A | | 9/1999 | Reichenbach et al. | 604/198 |
| 5,951,160 A | | 9/1999 | Ronk | 366/130 |
| 5,957,166 A | | 9/1999 | Safabash | 141/26 |
| 6,071,530 A | | 6/2000 | Polson et al. | 424/426 |
| 6,090,092 A | | 7/2000 | Fowles et al. | 604/413 |
| 6,096,562 A | * | 8/2000 | Bunn et al. | 436/518 |
| 6,106,783 A | * | 8/2000 | Gamble | 422/102 |
| 6,136,273 A | * | 10/2000 | Seguin et al. | 422/99 |
| 6,139,530 A | | 10/2000 | Hiejima et al. | 604/140 |
| 6,143,276 A | | 11/2000 | Unger | 424/9.3 |
| 6,164,044 A | * | 12/2000 | Porfano et al. | 53/471 |
| 6,174,304 B1 | | 1/2001 | Weston | |
| 6,189,292 B1 | * | 2/2001 | Odell et al. | 53/425 |
| 6,197,194 B1 | | 3/2001 | Whitmore | |
| 6,221,854 B1 | * | 4/2001 | Radomsky | 514/54 |
| 6,223,786 B1 | | 5/2001 | Castellano | |
| 6,224,883 B1 | * | 5/2001 | Roskos et al. | 424/400 |
| 6,290,680 B1 | | 9/2001 | Forsberg et al. | 604/232 |
| 6,302,160 B2 | | 10/2001 | Castellano | |
| 6,364,865 B1 | | 4/2002 | Lavi | 604/411 |
| 2001/0042317 A1 | | 11/2001 | Yarborough et al. | 34/287 |

FOREIGN PATENT DOCUMENTS

| | | | |
|---|---|---|---|
| DE | 19751226 | 1/1999 | B65B/3/04 |
| EP | 0242956 | 10/1987 | A61M/5/28 |
| EP | 0430474 | 6/1991 | A61K/9/70 |
| EP | 0539751 | 5/1993 | A61K/9/00 |
| EP | 0743072 | 11/1996 | A61M/5/315 |
| FR | 1109316 | 1/1956 | 19/4 |
| JP | 5-504941 | 7/1993 | A61K/6/00 |
| JP | 6-196132 | 7/1994 | H01J/65/04 |
| WO | 91/01126 | 2/1991 | A61K/6/00 |
| WO | 97/11155 | 3/1997 | C12M/1/00 |

* cited by examiner

COVER PLATE FOR USE IN LYOPHILIZATION

BACKGROUND OF THE INVENTION

Organic compounds, and more specifically pharmaceuticals, are generally more stable when they exist as a solid or powder than when they exist in solution. The shelf-life of a pharmaceutical stored in solution is generally shorter than the shelf-life of the pharmaceutical stored as a solid or powder. Since many pharmaceuticals are stored for extended periods of time before use, it is advantageous to have these pharmaceuticals remain active over the extended period of time. It is therefore desirable to store pharmaceuticals, over an extended period of time, as a solid or powder. This especially includes those pharmaceuticals that are ultimately reconstituted as a solution before administration.

Lyophilization is routinely used in the preparation and storage of pharmaceuticals. In such applications, lyophilization is usually carried out by freezing a solution containing the pharmaceutical, followed by sublimation to provide the solid or powder essentially free of solvent. Lyophilization directly in a vial or ampule requires transfer of the reconstituted pharmaceutical from the vial or ampule to a syringe. As such, a syringe is especially useful for the lyophilization of an injectable medication since the medication is ultimately administered from the syringe. Lyophilization can be performed wherein the solution containing the pharmaceutical is lyophilized directly in a syringe. See, U.S. application Ser. No. 09/190,341. The lyophilized pharmaceutical (i.e., medication) can then be stored in the syringe wherein a diluent can be added to the syringe for reconstitution of the medication just prior to administration. The medication can then be administered from the syringe directly to the patient.

Even though lyophilization of a solution directly in a syringe is useful, there exist serious drawbacks. Lyophilization typically results in the solution "popping" when there is a residual amount of solvent remaining. The popping can result in solvent and pharmaceutical being displaced outside the syringe. In addition, the popping can result in cross contamination of adjacent syringes in the array. When lyophilization is performed directly in a syringe, a significant amount of solution containing the pharmaceutical can be displaced outside the syringe. Accordingly, one cannot be certain whether any such pharmaceutical has been displaced outside the syringe and therefore the amount of pharmaceutical remaining inside the syringe after lyophilization may not be sufficiently accurate or precise. Thus, the syringe and the contents therein must be recycled or discarded since the amount of pharmaceutical remaining in the syringe cannot be adequately ascertained for proper administration.

Alternatively, a pharmaceutical can be introduced into a syringe directly as a solid or powder. The syringe is usually filled with the pharmaceutical with the use of powder filling equipment. The existing powder filling equipment, however, is not sufficiently accurate or precise to dispense a small amount of pharmaceutical necessary for administration. As such, there is a need for an apparatus that will allow for a relatively precise and accurate amount of pharmaceutical to be introduced into a syringe from a precise and accurate amount of solution containing the pharmaceutical.

SUMMARY OF THE INVENTION

The present invention provides a cover plate suitable for use to cover one or more delivery containers (e.g., syringe) during lyophilization. The cover plate of the present invention includes a lid region and one or more protuberances which project perpendicularly from the lid region. The one or more protuberances are adapted to fit in the one or more delivery containers. The cover plate permits the escape of vapor from the one or more delivery containers during the lyophilization process. In addition, the cover plate prevents the escape of lyophilizate from the one or more delivery containers during the lyophilization process.

The present invention also provides a system for lyophilizing a pharmaceutical solution. The system includes one or more delivery containers suitable for containing the pharmaceutical solution. The system also includes a cover plate of the present invention.

The present invention also provides another system for lyophilizing a pharmaceutical solution. The system includes a lyophilizing apparatus and one or more delivery containers. At least one of the one or more delivery containers contains the pharmaceutical solution. The system also includes a cover plate of the present invention that covers the one or more delivery containers during the lyophilization process.

The present invention also provides a method for lyophilizing a pharmaceutical solution. The method includes depositing the solution in one or more delivery containers, covering the one or more delivery containers with a cover plate of the present invention, and lyophilizing the solution that includes the pharmaceutical. The cover plate allows pharmaceutical solutions to be lyophilized while preventing cross contamination of adjacent syringes. In addition, the cover plate allows pharmaceutical solutions to be lyophilized while the amount of lyophilizate remaining inside the delivery containers is sufficiently ascertainable.

DETAILED DESCRIPTION OF THE INVENTION

The present invention provides a cover plate used to cover one or more delivery containers during the lyophilization of a solution. The cover plate of the present invention allows for the lyophilization of a solution in a delivery container whereby the solution and the lyophilizate remains inside the delivery container. During the lyophilization process employing the cover plate of the present invention, no significant amount of solution or lyophilizate is displaced outside the delivery container. As such, the amount of lyophilizate remaining inside the delivery container is sufficiently ascertainable. In addition, the use of the cover plate of the present invention during the lyophilization prevents cross-contamination of adjacent syringes in the array.

As used herein, "lyophilization" is the removal of solvent from the frozen state by sublimation. Lyophilization is accomplished by freezing the solution below its melting point and then manipulating the temperature and pressure to provide sublimation. Precise control of temperature and pressure permits drying from the frozen state without product melt-back. In practical applications, the process is accelerated and more precisely controlled under reduced pressure conditions. McGraw-Hill Concise Encyclopedia of Science & Technology, Fourth Edition, Sybil P. Parker, 1997.

As used herein, "lyophilizate" is the solid, powder or granular material remaining after lyophilization. The solid, powder or granular material is essentially free of solvent.

Figure 1:
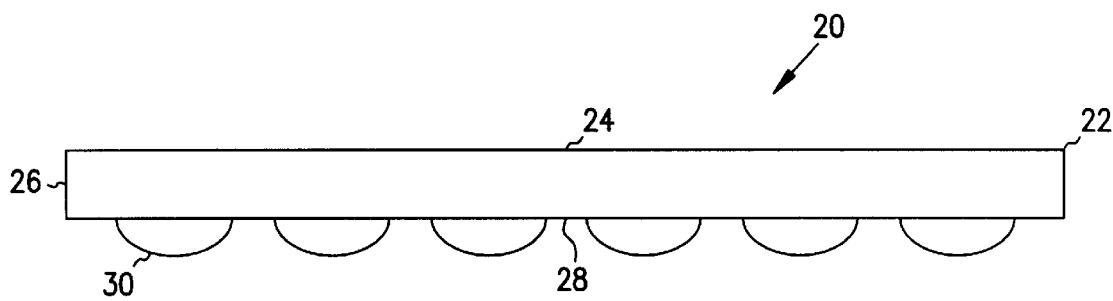
FIG. 1 is a side view of a cover plate wherein the protuberances are pointing downward.
Figure 2:
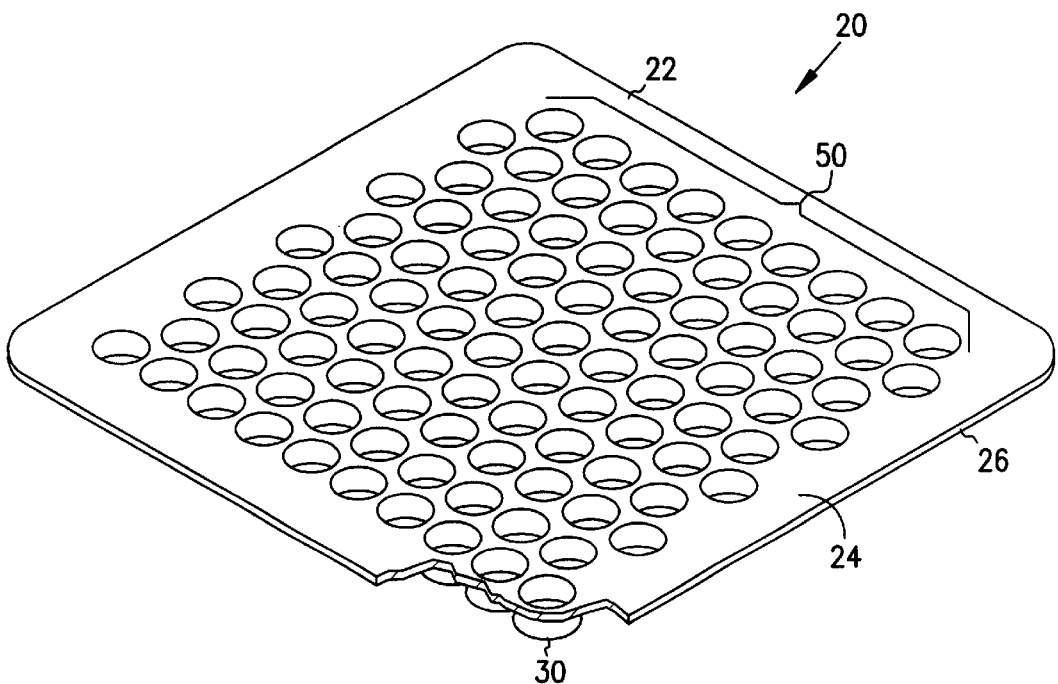
FIG. 2 is an illustration of a cover plate wherein the protuberances are pointed downward.
Figure 3:
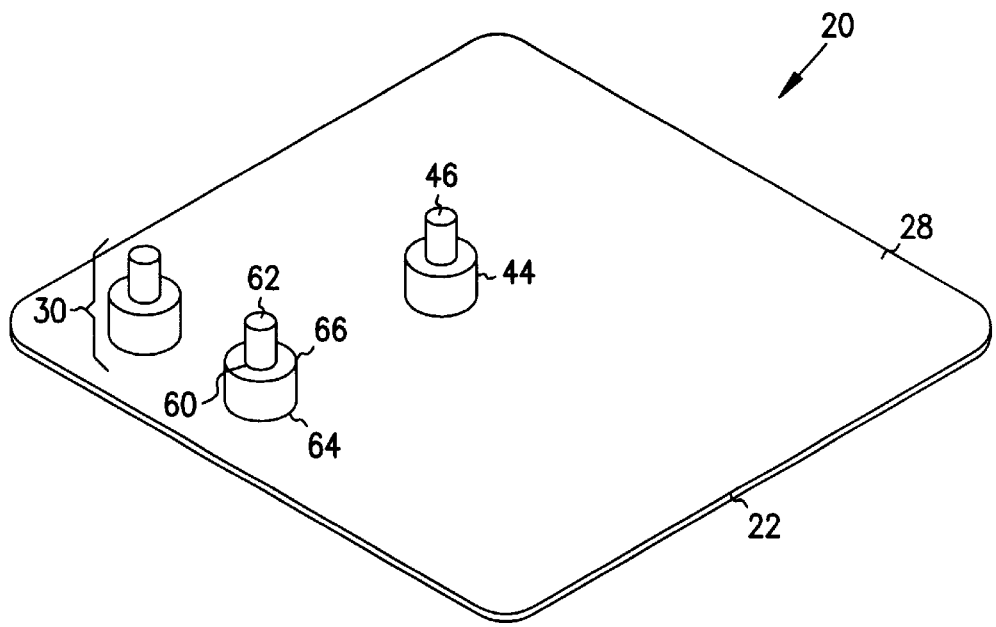
FIG. 3 is an illustration of a cover plate wherein the protuberances are pointing upward.

Referring to FIGS. 1–3, 7–8 and 11, a cover plate of the present invention is identified generally by the numeral 20. As shown in FIGS. 1–3, the cover plate 20 includes a lid region 22 and one or more protuberances 30. The lid region 22 includes an upper face 24, a middle section 26, and a lower face 28. The upper face 24 of the lid region 22 generally faces upward when the cover plate 20 is placed atop the delivery containers 4. The lower face 28 of the lid region 22 is opposite the upper face 24 and generally faces downward when the cover plate 20 is placed atop the delivery containers 4. The middle section 26 of the lid region 22 is the portion of the lid region 22 that separates the upper face 24 and the lower face 28. The upper face 24 does not come into contact with the delivery container 4 or the lyophilizate during lyophilization.

The cover plate 20 can have any suitable weight, shape and size provided the cover plate prevents the escape of lyophilizate from the delivery container 4 during lyophilization and permits the passage of vapor from the delivery container 4 during lyophilization. The size and shape of the cover plate 20 can correspond to the arrangement and number of protuberances 30 which can correspond to the arrangement and number of delivery containers 4. The cover plate 20 should be sufficiently light as to permit the passage of vapor from the delivery container 4 during lyophilization but should be sufficiently heavy as to not disengage from the delivery container 4 during lyophilization.

The lid region 22 can take any suitable shape. In addition, the upper face 24 and lower face 28 generally can take any suitable shape. The upper face 24 and lower face 28 can, for example, be essentially flat. The lid region 22 generally should be sufficiently thick as to facilitate easy handling and should be sufficiently durable for repeated uses. The lid region 22 is sufficiently thin and light, however, as to permit water vapor to escape during lyophilization, i.e., the lid region 22 is sufficiently thin and light as not to cause an air tight seal between any of the protuberances 30 and any of the corresponding delivery containers 4.

The cover plate 20 can be constructed to be slightly larger than the periphery 14 of the receptacle 6 of delivery containers 4 (see FIG. 4 and FIG. 11), such that the cover plate 20 can cover the entire receptacle 6. The cover plate 20 can be constructed to have the same general shape of the receptacle 6, such that the portion of the cover plate 20 overhanging the periphery 14 of the cover plate 20, if any, is not excessive or bulky in size. The cover plate 20 can be shaped to be smaller than the periphery 14 of the receptacle 6, as long as the cover plate 20 covers all of the delivery containers 4 to be lyophilized. The cover plate 20 can fit inside the periphery 14 of the receptacle 6 and can fit on an inside ledge 90 of the receptacle 6.

The cover plate 20 can be constructed from any suitable material. The material should be resistant to the temperature and pressure changes that exist during the lyophilization process. In addition, the material should be durable, inexpensive, and reusable. Suitable materials include plastics, TEFLON®, rubber, fiberglass, glass, and any combination thereof. Plastic is one preferable material for making the cover plate 20, as it is relatively light, durable, easy to use and relatively inexpensive.

Figure 7:
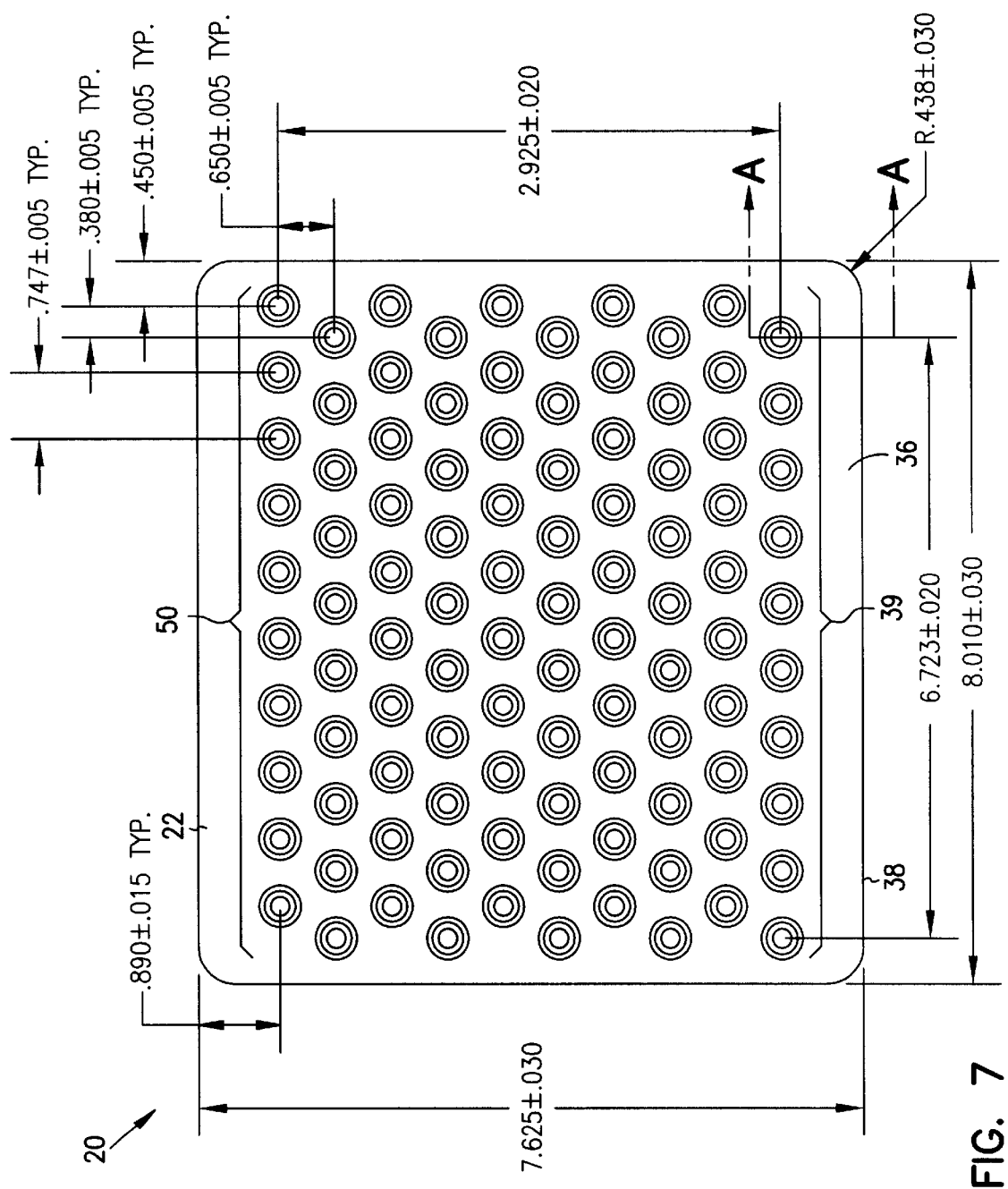
FIG. 7 is a top plan view of a cover plate, wherein the units of measurement are inches.
Figure 8:
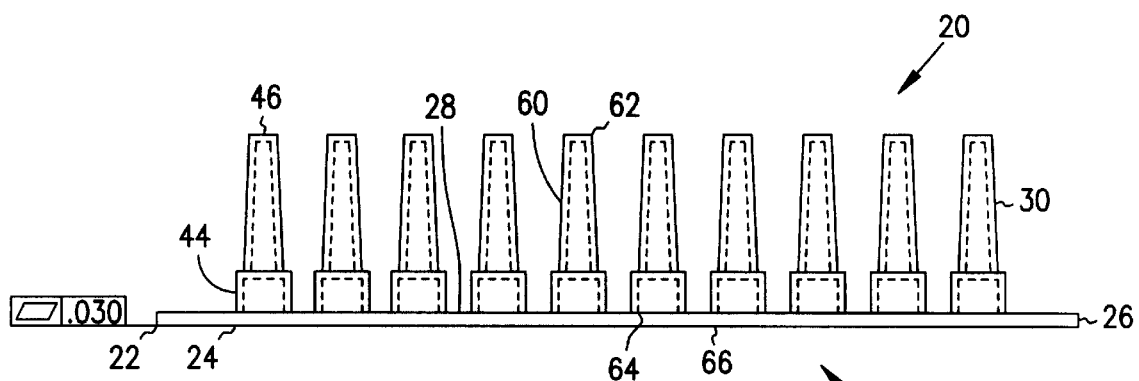
FIG. 8 is a side view of a cover plate illustrating a row of protuberances.

The cover plate 20, as illustrated in FIGS. 7 and 8, can be constructed to fit with the Hypak® or Steripak® configuration of prepackaged syringes in a tub 8 sold by Becton, Dickinson & Company. Specifically, the length of the cover plate 20, as illustrated in FIG. 7, can be about 7.6 inches to about 8.4 inches, and more specifically can be about 7.9 inches to about 8.1 inches. The width of the cover plate 20, as illustrated in FIG. 7, can be about 7.2 inches to about 8.0 inches, and more specifically can be about 7.5 inches to about 7.6 inches. The thickness of lid region 22 of cover plate 20, as illustrated in FIG. 7, can be between about 0.005 inches and about 0.2 inches, and more specifically can be about 0.020 inches to about 0.080 inches.

Figure 9:
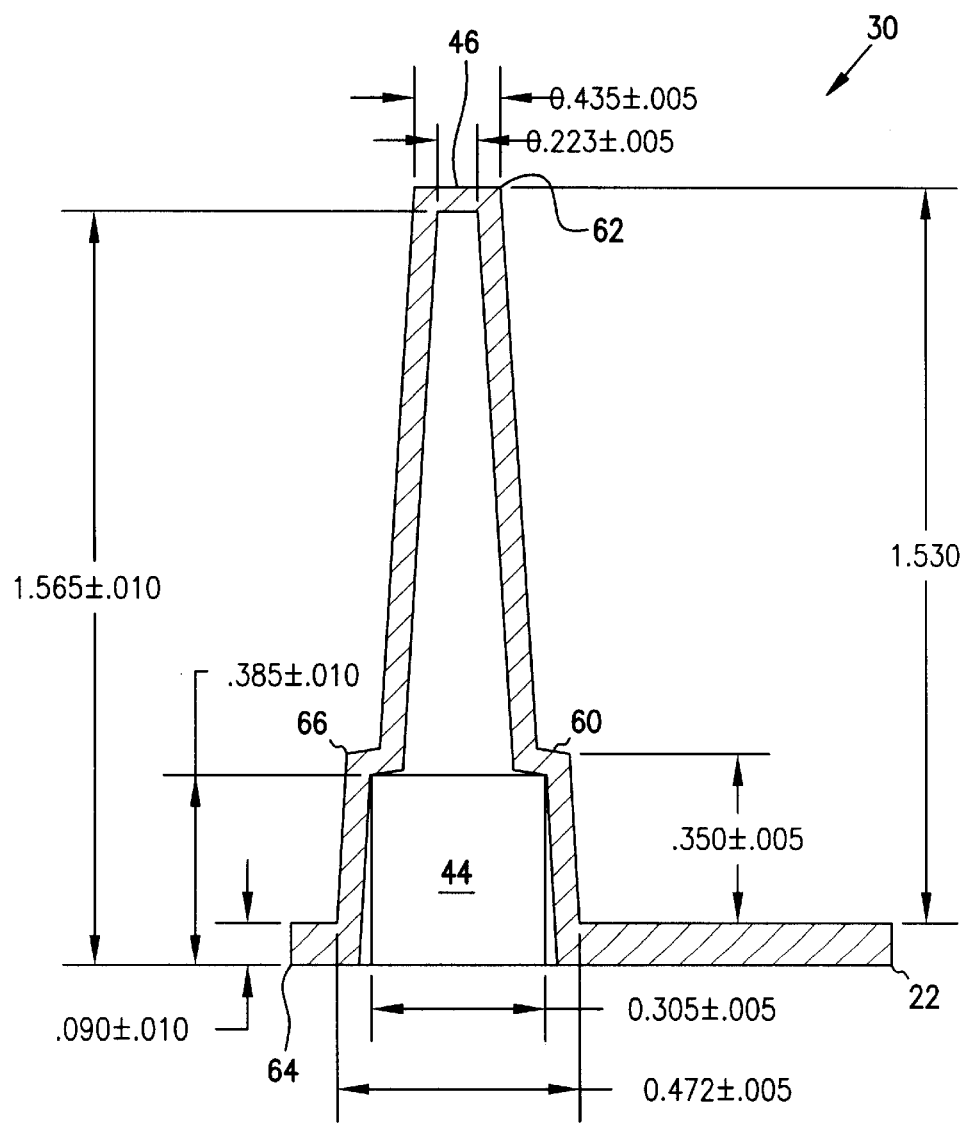
FIG. 9 is a side view of a protuberance, wherein the units of measurement are inches.

The cover plate 20 can include one or more protuberances 30. Specifically, the cover plate can include 1 to about 300, 1 to about 200, 50 to about 150 or about 75 to about 125 protuberances 30. As used herein, a "protuberance" is an object that bulges out from an adjacent surface (i.e., lid region 22). As shown in FIGS. 3 and 8–9, a protuberance 30 can project perpendicularly from the lid region 22. Any suitable protuberance can be employed in the present invention. Suitable protuberances can serve as a non air-tight stopper, plug or cap over a delivery container 4, thereby preventing the escape of lyophilizate from the delivery container 4 during lyophilization. In addition, suitable protuberances can catch lyophilizate that contacts the protuberance 30 during lyophilization. Accordingly, a suitable protuberance 30 prevents lyophilizate from one delivery container 4 from being introduced into another delivery container 4 during lyophilization, thereby contaminating the contents of one delivery container 4 with the contents of another delivery container 4. In addition, a suitable protuberance 30 permits lyophilization to proceed by allowing vapor to pass from the interior of the delivery container 4 to the exterior of the delivery container 4 during lyophilization.

Figure 4:
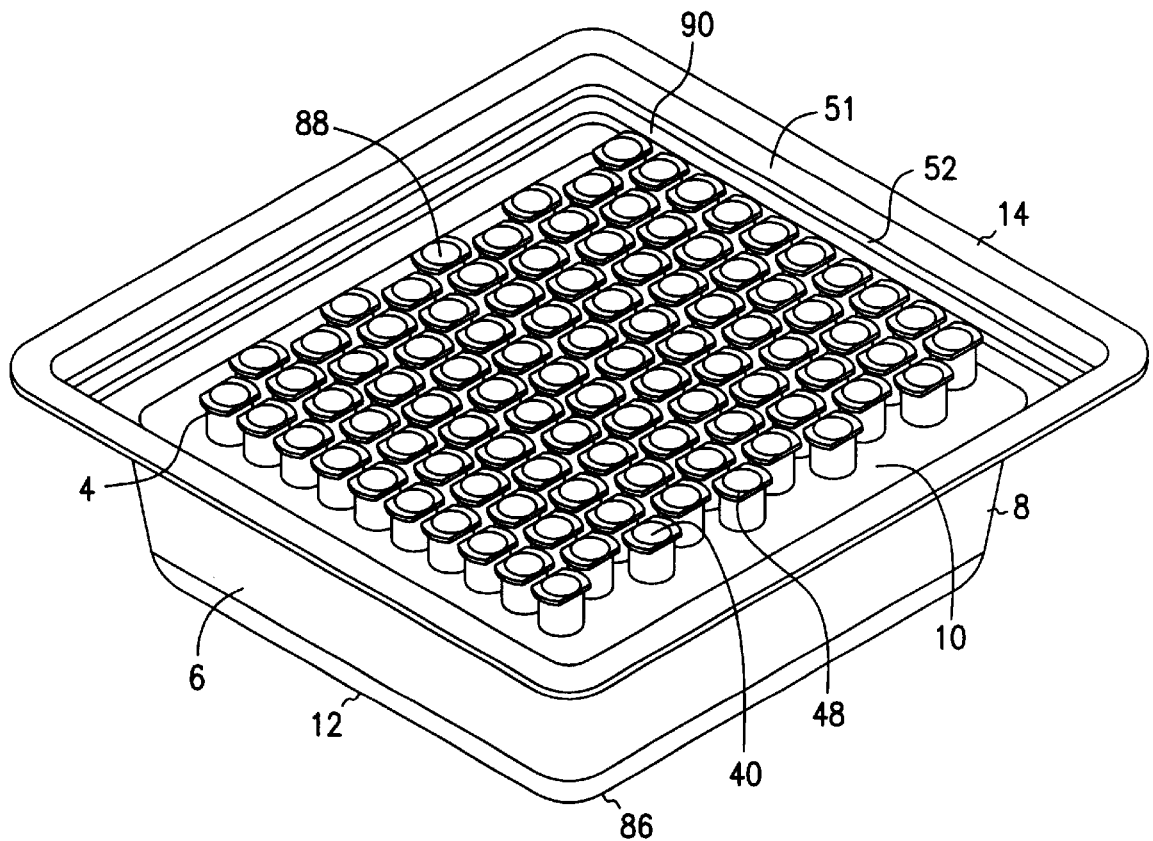
FIG. 4 is an illustration of a cover plate containing an array of syringes in a rack which is placed in a tub.
Figure 5:
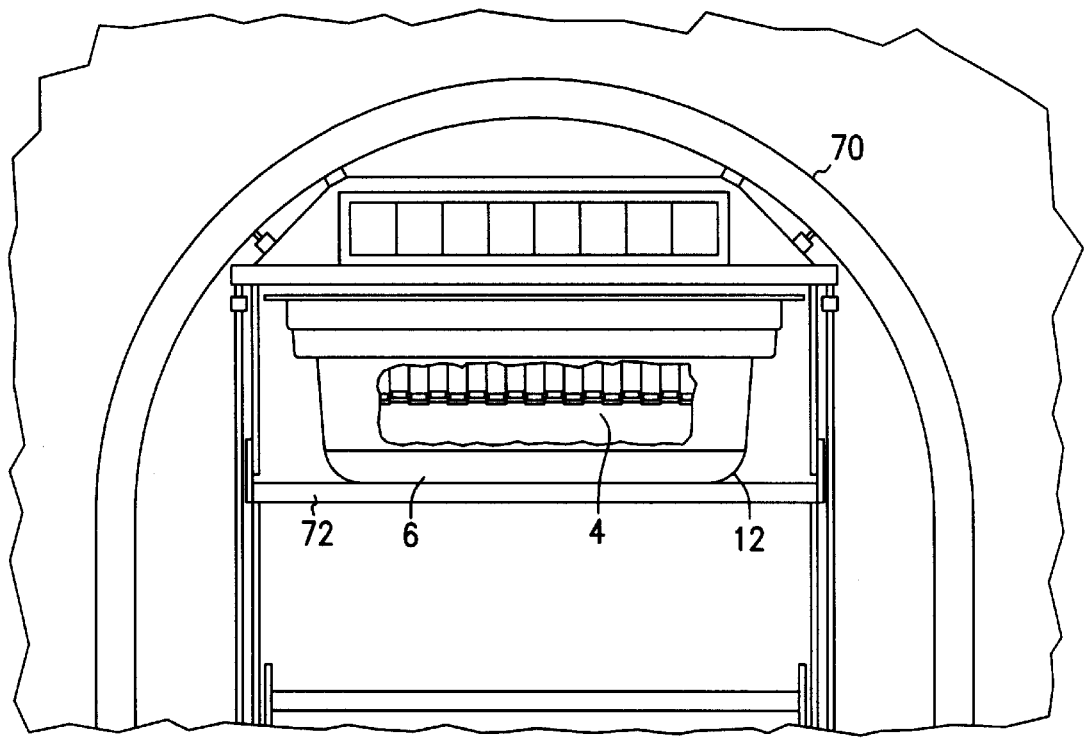
FIG. 5 is a frontal, partial cut-away view of an array of syringes in a rack which placed in a tub, which is placed in a lyophilizing apparatus.
Figure 10:
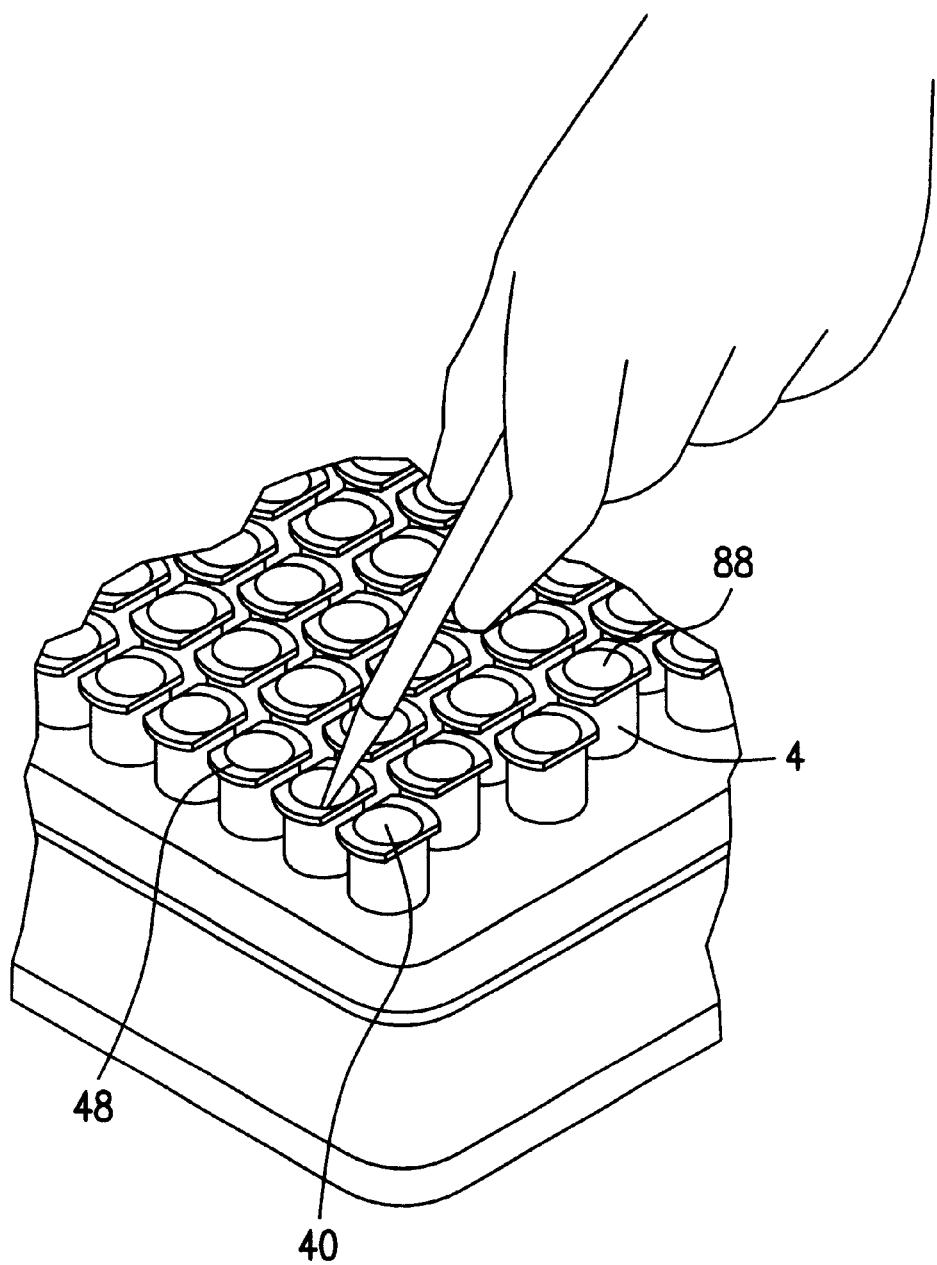
FIG. 10 is a perspective view of a solution being put into a syringe on a rack in a tub.
Figure 11:
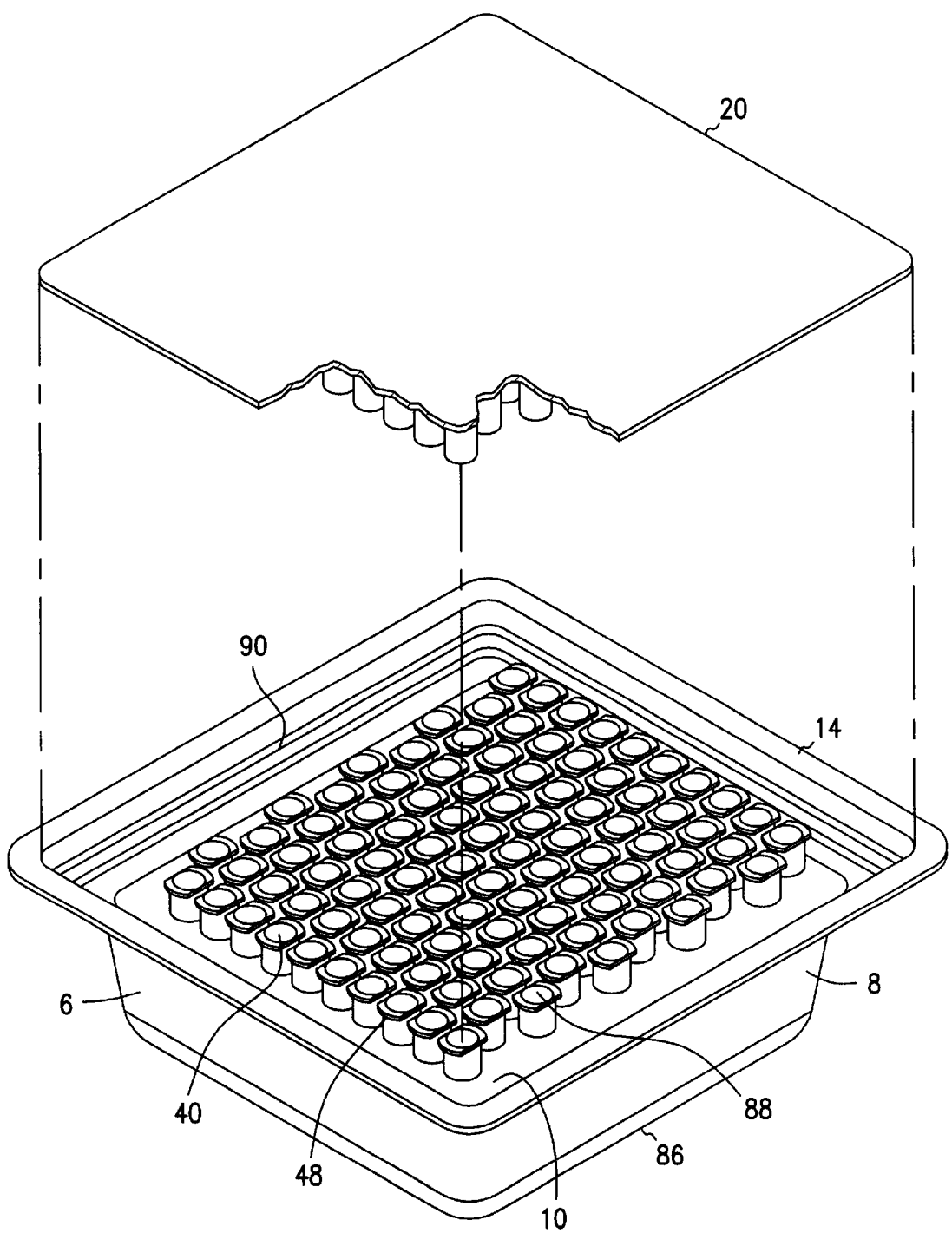
FIG. 11 is a perspective view of a cover plate being used to cover a tub of syringes.

The protuberance 30 can fit within the opening 40 of the delivery container 4 to prevent the escape of lyophilizate from the delivery container 4 and to allow vapor to pass from the interior of the delivery container 4 to the exterior of the delivery container 4 during lyophilization (see, FIGS. 4 and 10–11). As such, the protuberance 30 can have any suitable shape. The protuberance 30 can assume any suitable shape which corresponds with the shape of the opening 40 of the delivery container 4, so long as the protuberance 30 cooperates with the opening 40 of the delivery container 4. The protuberance 30 may be shaped in any suitable manner provided it caps or plugs the opening 40 of the delivery container 4 and permits the passage of vapor during lyophilization. As such, the shape of the protuberance 30 can depend upon the shape of the opening 40 of the delivery container 4.

Specifically, the protuberance 30 can be spherically shaped, conically shaped, or cylindrically shaped as shown in FIGS. 1, 8, and 3, respectively. In addition, the cylindrically shaped protuberance 30 can be tapered (see, e.g., FIGS. 8–9). The protuberance 30 can be tapered from the lower face 28 of the lid region 22 to lowest point vertically on the protuberance 30 after the cover plate 20 is placed atop the tub 8. Alternatively, protuberance 30 can be tapered from the lowest point vertically on the protuberance 30 after the cover plate 20 is placed atop the tub 8 to the lower face 28 of the lid region 22.

The protuberance 30 can fit cooperatively within the opening 40 of a delivery container 4. If the delivery container 4 is cylindrically-shaped, for example, like a syringe 42, the opening 40 of the delivery container 4 can be spherically shaped. As such, the protuberance 30 can be spherically shaped, conically shaped, or cylindrically shaped.

As used herein, "cylindrically shaped" is any shape having the approximate surface or portion thereof generated by a straight line moving parallel to a fixed straight line and intersecting a plane curve; "spherically shaped" is any shape having the approximate surface or portion thereof generated wherein all points are equidistant from a fixed point; and "conically shaped" is any shape having the approximate surface or portion thereof generated by a straight line, passing through a fixed point, and moving along the intersection with a fixed curve.

The cover plate 20 can contain a grid or array 51 of protuberances 30, as shown for example in FIGS. 3, 4, 7, and 8 so that the cover plate 20 can cover a number of delivery containers 4 being lyophilized at once (see, FIG. 11).

The protuberance 30 can protrude into the opening 40 of the delivery container 4 in a shape and to a degree to enhance the ability of the protuberance 30 to fit relatively snugly within the opening 40 of the delivery container 4. Accordingly, during lyophilization, the protuberances 30 can prevent the cover plate 20 from disengaging the delivery container 4. The length of each protuberance 30, as measured from the place at which the protuberance 30 attaches to the lower face 28 of the lid region 22 to the lowest point vertically on the protuberance 30 after the cover plate 20 is placed atop the tub 8, can vary, so long as the protuberance 30 captures lyophilizate, keeps the cover plate relatively firmly in place and permits the passage of vapor during lyophilization. The length can be, for example, as small as hundredths of an inch or as large as several inches, depending upon the size and depth of delivery containers 4. Generally, the longer the protuberances 30, the more firmly in place they will keep the cover plate 20 relative to the delivery containers 4 during lyophilization. The protuberances 30 should not be too long that they are too close to the contents of the delivery containers 4. In the example of this embodiment illustrated in FIG. 9, the length of each protuberance 30 can be about 1.0 inch to about 2.0 inches, and more specifically can be about 1.4 inches to about 1.6 inches.

The suitable length of the protuberance 30 can typically depend upon the length of the delivery containers 4 and the amount of contents in the delivery containers 4. Preferably, the suitable length of the protuberance 30 will minimize or lessen the occurrence of the contents of the delivery containers 4 from obtaining sufficient kinetic energy to pop or to be ejected out of the delivery containers 4. The suitable length of the protuberance 30 will minimize or lessen this occurrence by extending within about 0.5 inch, within about 0.25 inch, or within about 0.1 inch of the contents of the delivery containers 4.

The protuberance 30 can include an upper region 44 and a lower region 46 (see FIG. 8) which fit inside the opening 40 of a delivery container 4, and more particularly, the proximal opening 84 of a syringe 42. The upper region 44 can be cylindrically shaped. The lower region 46 can be conically shaped or cylindrically shaped.

Each upper region 44 can include an upper region top 64 and an upper region bottom 66. In addition, each lower region 46 can include a lower region top 60 and a lower region bottom 62. The upper region 44 can be tapered from the upper region top 64 to the upper region bottom 66. Likewise, the lower region 46 similarly can be tapered from the lower region top 60 to the lower region bottom 62. Accordingly, as shown in FIG. 8, the upper region 44 can be wider in diameter than the lower region 46, i.e., any cross-section of the upper region can be wider than any cross section of the lower region. The tapered shapes of the lower region 46 and the upper region 44 can be advantageous. Such shapes can more efficiently allow the escape of vapor from the delivery container 4 during lyophilization, while simultaneously capturing lyophilizate and ensuring that the cover plate 20 does not sufficiently move during lyophilization.

Figure 6:
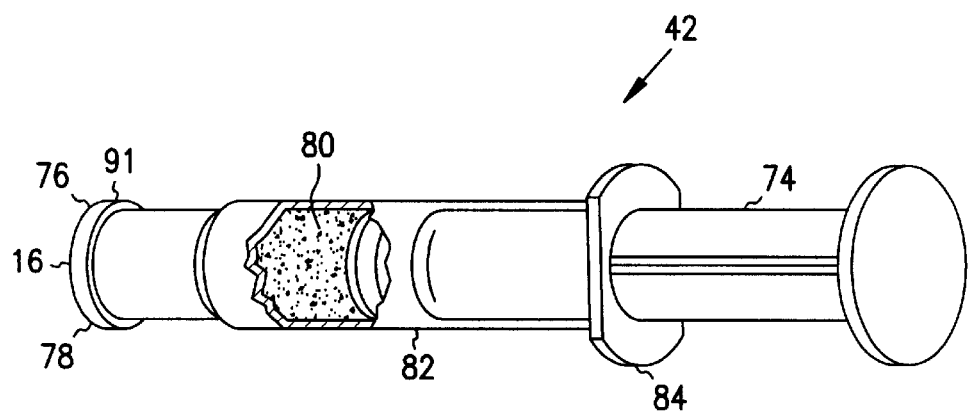
FIG. 6 is a perspective, partial cut-away view of a syringe containing lyophilized medication.

The shape of the upper region 44 can create a space or gap between the outer periphery 91 of distal end 78 of the syringe 42 (see FIG. 6) and the lower face 28 of the lid region 22, increasing the ease with which vapor can pass from the interior of the syringes 42 to the exterior of the syringes 42 during lyophilization. The protuberance 30 of the cover plate 20, including the optional upper regions 44, can be hollow, if desired, to minimize the weight of and the amount of material needed to manufacture the cover plate 20.

In one specific embodiment, as illustrated in FIGS. 7–9, the length of the upper region 44 can be about 0.10 inch to about 0.80 inch, and more specifically, can be about 0.30 inch to about 0.40 inch. The length of the lower region 46 can be about 1.0 inches to about 1.5 inches, and more specifically can be about 1.1 inches to about 1.2 inches.

The protuberances 30 can be spaced and positioned from each other so as to allow each to fit inside a set of commercially-available prepackaged, pre-sterilized syringes. The protuberances 30 can be positioned in a grid or array-like fashion, such as shown in FIGS. 2 and 7, to accommodate corresponding sets of syringes 42.

In one specific embodiment of the present invention, as illustrated in FIGS. 7 and 8, the distance between axial centers of adjacent protuberances in the same row, can be about 0.5 inch to about 0.9 inch, and more specifically can be about 0.6 inch to about 0.7 inch. The distance horizontally between axial centers of the nearest two protuberances 30 in adjacent rows, can be about 0.25 inch to about 0.5 inch, and more specifically can be about 0.3 inch to about 0.4 inch. The distance horizontally between axial centers of the nearest two protuberances 30 in adjacent rows, can be about 0.4 inch to about 0.9 inch, and more specifically can be about 0.6 inch to about 0.7 inch.

The lid region 22 can contain an outer perimeter region 36 extending from the outer edge 38 of the lid region 22 to each outer row of protuberances 30, to allow the cover plate 20 to rest on the ledge 52 of the tub 8. In one specific embodiment, as illustrated in FIG. 7, the width of the perimeter region can be about 0.6 inch to about 1.2 inch, and more specifically can be about 0.8 inch to about 0.9 inch.

The width of the perimeter region can be about 0.2 inch to about 0.7 inch, and more specifically can be about 0.3 inch to about 0.4 inch.

The cover plate can be used to lyophilize a solution containing a pharmaceutical in a delivery container. Any suitable pharmaceutical can be employed. Suitable pharmaceuticals include substances capable of prevention an infection systemically in an animal or human, or locally at the defect site, for example, antibacterial agents such as penicillin, cephalosporins, bacitracin, tetracycline, doxycycline, gentamycin, quinolines, neomycin, clindamycin, kanamycin, and metronidazole; anti-inflammatory agents such as hydrocortisone, and prednisone; antiparasitic agent such as quinacrine, chloroquine, and vidarbine; antifungal agents such as nystatin; antiviral agents such as acyclovir, ribarivin, and interferons; analgesic agents such as salicylic acid, acetaminophen, ibuprofen, naproxen, piroxicam, flurbiprofen, and morphine; local anesthetics such as cocaine, lidocaine, bupivacaine and benzocaine; immunogens (i.e., vaccines) for simulating antibodies against hepatitis, influenza, measles, rubella, tetanus, polio, and rabies; peptides such as an LH-RH agonist (e.g., leuprolide acetate), nafarelin, ganirelix, and goserelin.

Other suitable pharmaceuticals include substances, or metabolic precursors thereof, which are capable of promoting growth and survival of cells and tissues or augmenting the functioning of cells. Suitable compounds capable of promoting growth and survival of cells and tissues or augmenting the functioning of cells include a nerve growth promoting substance, such as a ganglioside or a nerve growth factor; a hard or soft tissue growth promoting agent, such as fibronectin (FN), human growth hormone (HGH), a colony stimulating factor, bone morphogenic protein, platelet-derived growth factor (PDGF), insulin-derived growth factor (IGF-I, IGF-II), transforming growth factor-alpha (TGF-α), transforming growth factor-β(TGF-β), epidermal growth factor (EGF), fibroblast growth factor (FGF), interleukin-1 (IL-1), and prostaglandins such as $PGE_1$, $PGE_2$ and $PGD_2$; an osteoinductive agent or bone growth promoting substance such a bone chips or demineralized bone material; and antineoplastic agents such as methotrexate, 5-fluouracil, adriamycin, vinblastine, cisplatin, tumor-specific antibodies conjugated to toxins, and tumor necrosis factor.

Other suitable pharmaceuticals include hormones such as progesterone, testosterone, follicle simulating hormone (FSH) (used for birth control and fertility-enhancement), insulin, and somatotropins; antihistamines such as diphenhydramine and chlorphencramine; cardiovascular agents such as digitalis, nitroglycerine, papaverine and streptokinase; anti-ulcer agents such as cimetidine hydrochloride, and isopropamide iodide; bronchodilators such as metaprotemal sulfate and aminophylline; vasodilators such as theophylline, niacin and minoxidil; central nervous system agents such as tranquilizer, b-adrenergic blocking agents, and dopamine; antipsychotic agents such as risperidone and olanzapine; narcotic antagonists such as naltrexone, naloxone and buprenorphine.

Additional suitable pharmaceuticals are provided in U.S. Pat. No. 5,234,529, the disclosure of which is incorporated by reference herein.

The pharmaceutical can optionally include a suitable excipient. Suitable excipients include ionic and non-ionic (amphoteric) surfactants (e.g., polysorbates, cremophores and tyloxopols), bulking agents (e.g., sodium phosphates, potassium phosphates, citric acid, tartaric acid, gelatins, and carbohydrates such as dextrose, mannitol and dextran), and lyoprotectants (e.g., glucose, catalase, maltose, maltotriose and maltohexose).

The delivery container 4 includes any receptacle in which a pharmaceutical can be lyophilized. Specifically, the delivery container 4 can be an ampule, vial, or syringe 42. Syringes are specifically suitable for lyophilizing pharmaceuticals whose ultimate use will be administration from a syringe. The pharmaceutical can reconstituted, if necessary, in the syringe in which the pharmaceutical was lyophilized. Accordingly, syringes are especially suitable for lyophilizing an injectable pharmaceutical (i.e., medication), since the medication is ultimately administered from the syringe.

The syringe 42 can be manufactured from any suitable material. Suitable materials are those materials that are resistant to the temperature and pressure changes that exist during the lyophilization process. The material can be durable and inexpensive. Suitable materials include plastics, glass, and any combination thereof.

Specifically, the syringe can be manufactured from plastic. Plastic syringes are generally stronger than glass syringes. The increased strength of plastic results in a more durable syringe. The increased durability allows for a safer syringe as a plastic syringe will not break as easily upon administration as compared to a glass syringe. As such, fewer health care professionals will become injured while reconstituting and administering injectable medications in a plastic syringe as compared to a glass syringe.

Due to the increased strength of plastic syringes, the bore size of plastic syringes are routinely larger than those of comparable glass syringes, thereby decreasing the force required to use the plastic syringe. This is especially useful when reconstituting an injectable medication with a very viscous diluent or for syringe-to-syringe reconstitution. See, U.S. patent application Ser. No. 09/405,463 filed on Sep. 24, 1999.

The syringe can be disposable or can be reusable. Disposable syringes are commercially available and are usually constructed from plastic or glass. Disposable syringes are popular due to their convenience and because they are relatively inexpensive. A suitable disposable plastic syringe of the present invention is manufactured by Becton Dickinson & Company in what is known as a "Hypak" configuration and is disclosed in U.S. Pat. No. 4,758,230.

The delivery container 4 can be loaded vertically into a rack 10 in a receptacle 6, such as a plastic tub 8, so the solution faces the bottom 86 of the tub 8 and the open end 88 of the delivery container 4 faces upward. When more than one delivery container 4 containing solution of pharmaceutical is being lyophilized concurrently, the multiple delivery containers 4 can be loaded into the rack 10 in the plastic tub 8. While the delivery container 4 may be filled with solution before being placed into the tub 8, the delivery container 4 can alternatively be placed in the tub 8 first and then the solution can be filled and lyophilized. That is, the delivery container 4 can be loaded into the plastic rack 10 in the plastic tub 8 and then can be filled with solution. As such, multiple delivery containers 4 can be lyophilized simultaneously.

As used herein a "receptacle" is any suitable vesicle capable of receiving a rack 10. Specifically, the receptacle is a tub 8. As used herein, a "tub" is a round, square or rectangular, open, flat-bottomed vessel, usually wider than tall and a "rack" is any suitable framework or stand in which to hold one or more delivery containers 4.

As used herein, a "lyophilizing apparatus" is any apparatus used to lyophilize a solution capable of being lyophilized. The apparatus can cool the solution to the frozen state or the apparatus can maintain the solution in the frozen state while the lyophilization is performed. In addition, the apparatus can reduce the pressure (i.e., create a partial vacuum) on the inside of the delivery container 4 and optionally on the outside of the delivery container 4 while the lyophilization is performed.

The solution containing the pharmaceutical can be cooled to a frozen solid prior to lyophilization. The solution can be cooled by any suitable cooling means (e.g., convention, conduction or radiation). Specifically, the solution can be cooled by convection.

After the solution is cooled to a frozen solid, a partial vacuum is applied to the lyophilizing apparatus 70 to provide a partial vacuum within the lyophilizing apparatus 70 (i.e., within the inside of the delivery container 4 and on the outside of the delivery container 4). The partial vacuum can be applied to the solution, in the frozen state, until essentially all of the solvent is removed (i.e., to dryness).

After lyophilization is completed, the tub 8 can be removed from the lyophilization apparatus 70. The cover plate 20 can be removed from the delivery container 4 and examined for any retained lyophilizate. If the protuberances 30 of the cover plate 20 contains any lyophilizate, each delivery container 4 from which the lyophilizate originated can be discarded or recycled and the lyophilizate can be recycled or discarded. If any pharmaceutical leaves a delivery container and is captured on the restrictor plate, the amount of lyophilized pharmaceutical remaining in the delivery container is unknown. Thus, any delivery container losing any lyophilizate captured by the cover plate can be discarded or recycled. Accordingly, the cover plate is removed from on top of the delivery container and examined for any retained lyophilizate. If the cover plate contains any lyophilizate, each delivery container from which the lyophilizate originated can be discarded or recycled.

After lyophilization, the opening 40 of any undiscarded delivery container 4 can be sealed for storage. The delivery container 4 can be sealed with any suitable sealing device known for sealing delivery containers 4. Where the delivery container 4 is a syringe 42, the proximal opening 84 of the syringe barrel 82 can be sealed with the plunger 74 of the syringe 42.

When ready for use, the seal can be removed from the delivery container 4 and diluent can be added to the delivery container 4 (e.g., syringe 42) for reconstitution. The lyophilized pharmaceutical can then be used. Where the delivery container 4 is a syringe 42, a cap 76 covering the distal end 78 of a syringe barrel 82 can be removed and a hypodermic needle can be inserted to the distal end 78 by screwing it on to threads which can receive the needle. The needle end of the syringe 42 can then be inserted into the receptacle containing the diluent, and the syringe plunger 74 can be withdrawn towards the proximal end 84 of the syringe barrel 82 until the appropriate amount of diluent is extracted into the syringe 42 for reconstitution. The syringe 42 can be withdrawn from the diluent-containing receptacle, and the contents of the syringe 42 can be mixed by agitation until the lyophilized cake is dissolved or suspended in the diluent. The reconstituted pharmaceutical can then be administered.

Each delivery container 4 to be lyophilized can be loaded into a receptacle 6, which in turn, is placed inside a lyophilizing apparatus 70. More typically, each delivery container 4 is loaded vertically into a plastic rack 10 in a tub 8, so the solution containing the pharmaceutical faces the bottom of the tub and the open end of each delivery container faces upward. If the delivery container is a syringe 42, the syringe 42 is loaded into the plastic rack in the tub 8, so the distal end 78 of the syringe 42, covered by a cap 76, faces the bottom of the tub 8 and the proximal end 84 of the syringe 42, faces upward. Alternatively, each delivery container 4 can be loaded in the tub 8 before depositing the solution containing pharmaceutical therein. After being loaded into the tub 8, each delivery container 4 in the tub 8 can be covered with a cover plate 20.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for lyophilizing a pharmaceutical solution comprising:

depositing the solution in one or more delivery containers;

covering the one or more delivery containers with a cover plate, the cover plate resting on the top of the one or more delivery containers, the cover plate comprising a lid region and one or more protuberances which project perpendicularly from the lid region, wherein the one or more protuberances are adapted to fit in the one or more delivery containers, wherein the cover plate permits the escape of vapor from the one or more delivery containers during the lyophilization process, through an annular gap between each protuberance and a side wall of each container when the cover plate is resting on the top of the one or more delivery containers, and wherein the cover plate prevents the escape of lyophilizate from the one or more delivery containers during the lyophilization process;

positioning the cover plate on the one or more delivery containers such that the one or more protuberances of the cover plate are positionally aligned with the one or more delivery containers, and placing the cover plate and the one or more delivery containers inside the lyophilizing apparatus or placing the one or more delivery containers and the cover plate inside the lyophilizing apparatus and positioning the cover plate on the one or more delivery containers such that the one or more protuberances of the cover plate are positionally aligned with the one or more delivery containers; and at least partially lyophilizing the solution comprising the pharmaceutical.

2. The method of claim 1 further comprising removing the cover plate from the one or more delivery containers after the lyophilizing.

3. The method of claim 1 wherein the lyophilizing is carried out until the pharmaceutical is free of solvent.

4. The method of claim 1 further comprising sealing the one or more delivery containers containing the pharmaceutical.

5. The method of claim 1 wherein the one or more delivery containers is a pre-packaged and pre-sterilized syringe.

6. The method of claim 5 wherein the syringe is positioned in a rack.

7. The method of claim 1, further comprising positioning an array of protuberances over the delivery containers.

8. The method of claim 1, further comprising positioning at least a portion of the length of the protuberances within the delivery containers.

9. The method of claim 1, further comprising positioning an entire length of the protuberances within the delivery containers.

10. The method of claim 1, further comprising positioning a tapered portion of the one or more protuberances within the delivery containers.

* * * * *